United States Patent [19]

Shutske et al.

[11] Patent Number: 4,753,950

[45] Date of Patent: Jun. 28, 1988

[54] FUSED HETEROCYCLIC TETRAHYDROAMINOQUINOLINOLS AND RELATED COMPOUNDS

[75] Inventors: Gregory M. Shutske, Somerset; Kevin J. Kapples, Bridgewater, both of N.J.

[73] Assignee: Hoechst-Roussel Pharmaceuticals, Inc., Somerville, N.J.

[21] Appl. No.: 934,038

[22] Filed: Nov. 24, 1986

[51] Int. Cl.$^4$ .................. A61K 31/47; C07D 471/04
[52] U.S. Cl. .................. 514/291; 514/292; 514/293; 546/80; 546/81; 546/82
[58] Field of Search .................. 546/80, 81, 82, 89; 514/291, 292, 293

[56] References Cited

U.S. PATENT DOCUMENTS 4,546,104 10/1985 Campbell et al. .................. 546/82

FOREIGN PATENT DOCUMENTS 0179383 4/1986 European Pat. Off. .................. 79/

OTHER PUBLICATIONS

Chemical Abstracts, vol. 103(25) Abst. No. 215280x, Dec. 23, 1985.
U.S.A. Today, Jul. 9, 1987, p. 2.
Nielsen et al., Liebigs Ann. Chem., 1986, pp. 1728–1735.
John et al., Drug Development Research, 1985, vol. 5, pp. 77–96.

Primary Examiner—Mary C. Lee
Assistant Examiner—Zinna Northington
Attorney, Agent, or Firm—Tatsuya Ikeda

[57] ABSTRACT

There are disclosed compounds of the formula

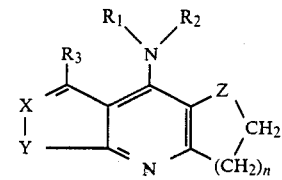

where $=X-Y-$ is

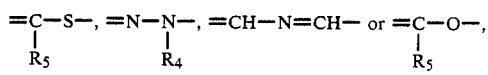

$R_4$ being loweralkyl and $R_5$ being hydrogen or loweralkyl, $-Z-$ is

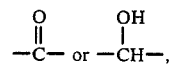

n is 1, 2 or 3, $R_1$ and $R_2$ are each independently hydrogen, loweralkyl or aryloweralkyl, and $R_3$ is hydrogen or loweralkyl, with the proviso that when $=X-Y-$ is

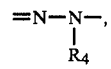

n is 2 or 3, $R_1$ is hydrogen and $R_2$ is hydrogen or loweralkyl, Z is not

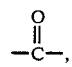

which compounds are useful for enhancing memory and for treating Alzheimer's disease.

20 Claims, No Drawings

FUSED HETEROCYCLIC TETRAHYDROAMINOQUINOLINOLS AND RELATED COMPOUNDS

The present invention is directed to compounds of the formula $$\begin{array}{c} R_1 \quad R_2 \\ R_3 \quad N \\ X \quad \quad Z \\ | \quad \quad CH_2 \\ Y \quad N \quad (CH_2)_n \end{array}$$

where =X—Y— is $$=C-S-, \quad =N-N-, \quad =CH-N=CH- \text{ or } =C-O-,$$
$$\quad | \quad \quad \quad | \quad \quad \quad \quad \quad \quad \quad \quad \quad |$$
$$\quad R_5 \quad \quad R_4 \quad \quad \quad \quad \quad \quad \quad \quad R_5$$

$R_4$ being loweralkyl and $R_5$ being hydrogen or loweralkyl, —Z— is $$\begin{array}{cc} O & OH \\ \| & | \\ -C- \text{ or } -CH-, \end{array}$$

n is 1, 2 or 3, $R_1$ and $R_2$ are each independently hydrogen, loweralkyl or arylloweralkyl, and $R_3$ is hydrogen or loweralkyl, with the proviso that when =X—Y— is $$=N-N-, \\ | \\ R_4$$

n is 2 or 3, $R_1$ is hydrogen and $R_2$ is hydrogen or loweralkyl, Z is not $$\begin{array}{c} O \\ \| \\ -C-, \end{array}$$

and pharmaceutically acceptable acid addition salts thereof which are useful for enhancing memory and for treating Alzheimer's disease; pharmaceutical compositions comprising an effective memory enhancing amount of such a compound and a method of treating a patient in need of memory enhancement which comprises administering such a compound to the patient.

Unless otherwise stated or indicated, the following definitions shall apply throughout the specification and the appended claims.

The term loweralkyl shall mean a straight or branched alkyl group having from 1 to 6 carbon atoms. Examples of said loweralkyl include methyl, ethyl, n-propyl, iso-propyl, n-butyl, iso-butyl, sec-butyl, t-butyl and straight- and branched-chain pentyl and hexyl.

The term halogen shall mean fluorine, chlorine, bromine or iodine.

The term aryl shall mean an unsubstituted phenyl group or a phenyl group substituted with 1, 2 or 3 substituent groups each of which being independently loweralkyl, halogen, loweralkoxy, or trifluoromethyl.

Throughout the specification and appended claims a given chemical formula or name shall include all optical isomers and mixtures thereof where such isomers exist.

The compounds of this invention are prepared by utilizing one or more of the steps described below.

In order to simplify the description of the synthetic schemes, the description will be presented with specific reference to the situation where n is 2, but it will readily be understood that the synthetic schemes can also be applied to the other situations where n is 1 or 3 by making obvious modifications where necessary.

Throughout the description of the synthetic steps, the notations, X, Y, Z, n, $R_1$, $R_2$, $R_3$, $R_4$ and $R_5$ shall have the respective meanings given above unless otherwise stated or indicated.

STEP A

A compound of formula II is reacted with a hydrazine derivative of formula III to afford a pyrazole derivative of formula IV.

$$\begin{array}{ccc} R_3 \quad CN & & R_3 \quad CN \\ \diagdown \quad \diagup & & \diagdown \diagup \\ \quad + NH_2NHR_4 \longrightarrow & N \\ \diagup \quad \diagdown & & \diagdown \diagup \\ EtO \quad CN & & N \quad NH_2 \\ & & | \\ & & R_4 \\ (II) \quad (III) & & (IV) \end{array}$$

Typically, this reaction is conducted in a suitable solvent such as loweralkanol including methanol and ethanol at 50°–150°. This type of reaction is disclosed, for instance, in Breuer et al., U.S. Pat. No. 3,732,335; Breuer and Treuner, U.S. Pat. No. 3,847,908; and Campbell et al., European Patent Application No. 0,141,608 (1985).

STEP B

A compound of formula V (which may exist in a dimer form) is reacted with malononitrile to afford a thiophene derivative of formula VI.

$$\begin{array}{ccc} R_3 \quad O & CN & R_3 \quad CN \\ \diagdown \diagup & | & \diagdown \diagup \\ \quad + CH_2 \longrightarrow & \\ \diagup \diagdown & | & \diagup \diagdown \\ R_5 \quad SH & CN & R_5 \quad S \quad NH_2 \\ (V) & & (VI) \end{array}$$

This reaction is conducted typically in the presence of a base such as triethylamine, trimethylamine, piperidine or pyrrolidine and a suitable solvent such as loweralkanol including methanol and ethanol or a tertiary amide including N,N-dimethylformamide, N,N-dimethylacetamide and N-methylpyrrolidinone at 50°–120° C. or the boiling point of the solvent. This type of reaction is disclosed, for instance, in K. Gewald, Chem. Ber. 98, 3571 (1965).

STEP C

A compound of formula VII (which may exist in a dimer form) is reacted with malononitrile to afford a furan derivative of formula VIII.

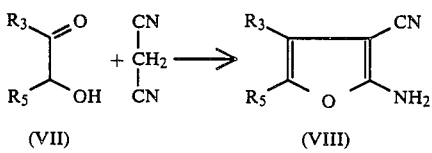

This reaction is conducted in substantially the same manner as in STEP B except that the temperature of the reaction mixture is maintained lower than 40° C. This type of reaction is disclosed, for instance, in K. Gewald, Chem. Ber. 99, 1002 (1966).

STEP D

A compound of formula IX is chlorinated with a chlorinating reagent such as phosphorus oxychloride, thionyl chloride or phosphorus pentachloride in a manner known to the art to afford a chloro derivative of formula X. Compound X is reacted with sodium azide in a manner known to the art to afford an azide derivative of formula XI. Compound XI is catalytically hydrogenated in the presence of palladium/carbon in a manner known to the art to afford a pyridine derivative of formula XII.

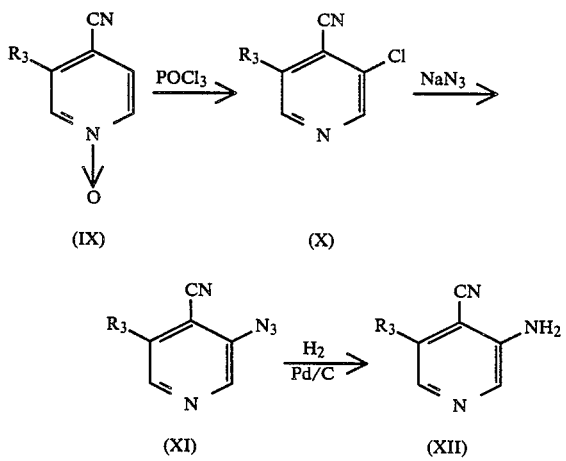

The above synthetic scheme is disclosed in J. Rokach and Y. Girard, J. Heterocyclic Chem., 15, 683 (1978) and J. L. La Mattina and R. L. Taylor, J. Org. Chem., 46, 4179 (1981).

STEP E

A compound of formula XIII obtained from STEP A, B, C or D described above is reacted with 1,3-cyclohexadione to afford an enamine derivative of formula XIV.

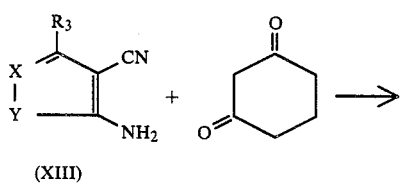

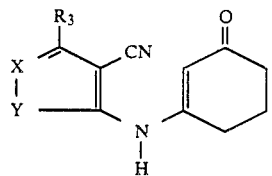

Typically, said reaction is conducted in a suitable solvent such as ethereal solvent including tetrahydrofuran, diethyl ether, diethyleneglycol dimethyl ether and dioxane or aromatic hydrocarbon including benzene and toluene at a temperature of about 30°–120° C.

STEP F

Compound XIV is cyclized to afford a compound of formula XV.

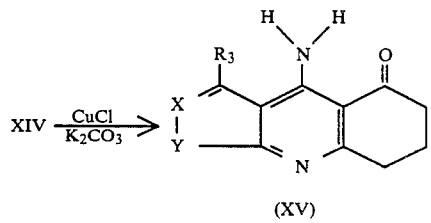

Said reaction is typically conducted by preparing a suspension comprising compound XIV, a base such as milled potassium carbonate, sodium carbonate or sodium hydride, a cuprous halide catalyst such as cuprous chloride, cuprous bromide or cuprous iodide and a suitable medium such as ethereal solvent including tetrahydrofuran, 1,4-dioxane and diethyleneglycol dimethyl ether and maintaining the reaction mixture at 50°–120° C. or under gentle reflux.

STEP G

Compound XV is allowed to react with a loweralkyl bromide or arylloweralkyl bromide of the formula ($R_1$ is not hydrogen) to afford a compound of formula XVI.

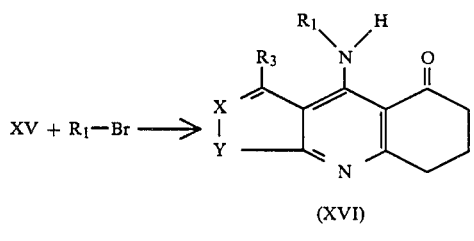

This reaction is typically conducted by preparing a solution of compound XV in a suitable solvent such as polar aprotic solvent including dimethylsulfoxide, N,N-dimethylformamide and N,N-dimethylacetamide, adding a base such as pulverized KOH, NaOH, NaH or potassium tertiary butoxide to the solution, stirring the mixture for a short period of time (15 minutes for instance) at 10°–40° C., adding the bromide compound and stirring the reaction mixture at 10°–40° C.

STEP H

Compound XVI is allowed to react with a loweralkyl bromide or arylloweralkyl bromide of the formula $R_2$—Br ($R_2$ is not hydrogen) to afford a compound of formula XVII.

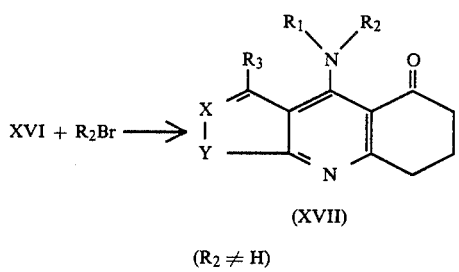

($R_2 \neq H$)

This reaction is conducted in substantially the same manner as in STEP G.

STEP I

A compound of formula XVIII (where $R_1$ and $R_2$ are each independently hydrogen, loweralkyl or arylloweralkyl) which is obtained from STEP F, G or I is reduced with $LiAlH_4$, $Al(iso-Bu)_2H$, $NaAlH_2(OCH_2CH_2OCH_3)_2$, $AlH_3$ or $LiB(sec-Bu)_3H$ to afford a compound of formula XIX.

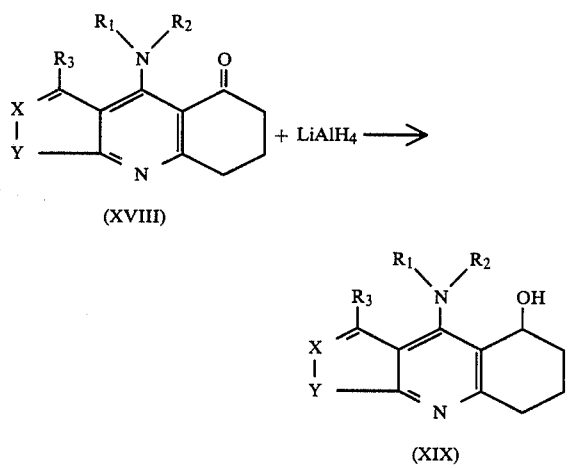

This reaction is typically conducted in a suitable medium such as anhydrous ethereal solvent including tetrahydrofuran, diethyl ether and ethyleneglycol dimethyl ether or aromatic hydrocarbon such as benzene or toluene and stirring the reaction mixture between $-10°$ C. and $30°$ C.

The compounds of formula (I) of the present invention are useful in the treatment of various memory dysfunctions characterized by decreased cholinergic function, such as Alzheimer's disease. This utility is demonstrated by the ability of these compounds to restore cholinergically deficient memory in the Dark Avoidance Assay.

Dark Avoidance Assay

In this assay mice are tested for their ability to remember an unpleasant stimulus for a period of 24 hours. A mouse is placed in a chamber that contains a dark compartment; a strong incandescent light drives it to the dark compartment, where an electric shock is administered through metal plates on the floor. The animal is removed from the testing apparatus and tested again, 24 hours later, for the ability to remember the electric shock.

If scopolamine, an anticholinergic that is known to cause memory impairment, is administered before an animal's initial exposure to the test chamber, the animal re-enters the dark compartment shortly after being placed in the test chamber 24 hours later. This effect of scopolamine is blocked by an active test compound, resulting in a greater interval before re-entry into the dark compartment.

The results for an active compound are expressed as the percent of a group of animals in which the effect of scopolamine is blocked, as manifested by an increased interval between being placed in the test chamber and re-entering the dark compartment. An example of test result is presented in Table 1 along with the results of prior art compounds.

TABLE 1

| | Dark Avoidance Assay | |
|---|---|---|
| Compound | Dose (mg/kg of Body Weight) | % of Animals With Scopolamine Induced Memory Deficit Reversed |
| 4-amino-5,6,7,8-tetra-hydrothieno[2,3-b]-quinolin-5-ol | 0.31 | 27 |
| (prior art compounds) | | |
| Tacrine | 0.63 | 13 |
| Pilocarpine | 1.25 | 19 |

Effective quantities of the compounds of the invention may be administered to a patient by any of the various methods, for example, orally as in capsules or tablets, parenterally in the form of sterile solutions or suspensions, and in some cases intravenously in the form of sterile solutions. The free base final products, while effective themselves, may be formulated and administered in the form of their pharmaceutically acceptable acid addition salts for purposes of stability, convenience of crystallization, increased solubility and the like.

Acids useful for preparing the pharmaceutically acceptable acid addition salts of the invention include inorganic acids such as hydrochloric, hydrobromic, sulfuric, nitric, phosphoric and perchloric acids, as well as organic acids such as tartarcic, citric, acetic, succinic, maleic, fumaric and oxalic acids.

The active compounds of the present invention may be orally administered, for example, with an inert diluent or with an edible carrier, or they may be enclosed in gelatin capsules, or they may be compressed into tablets. For the purpose of oral therapeutic administration, the active compounds of the invention may be incorporated with excipients and used in the form of tablets, troches, capsules, elixirs, suspensions, syrups, wafers, chewing gum and the like. These preparations should contain at least 0.5% of active compound, but may be varied depending upon the particular form and may conveniently be between 4% to about 70% of the weight of the unit. The amount of active compound in such compositions is such that a suitable dosage will be obtained. Preferred compositions and preparations according to the present invention are prepared so that an oral dosage unit form contains between 1.0–300 milligrams of active compound.

The tablets, pills, capsules, troches and the like may also contain the following ingredients: a binder such as micro-crystalline cellulose, gum tragacanth or gelatine;

an excipient such as starch or lactose, a disintegrating agent such as alginic acid, Primogel, cornstarch and the like; a lubricant such as magnesium stearate or Sterotex; a glidant such as colloidal silicon dioxide; and a sweetening agent such as sucrose or saccharin may be added or a flavoring agent such as peppermint, methyl salicylate, or orange flavoring. When the dosage unit form is a capsule, it may contain, in addition to materials of the above type, a liquid carrier such as a fatty oil. Other dosage unit forms may contain other various materials which modify the physical form of the dosage unit, for example, as coatings. Thus tablets or pills may be coated with sugar, shellac, or other enteric coating agents. A syrup may contain, in addition to the active compounds, sucrose as a sweetening agent and certain preservatives, dyes, coloring and flavors. Materials used in preparing these various compositions should be pharmaceutically pure and non-toxic in the amounts used.

For the purposes of parenteral therapeutic administration, the active compounds of the invention may be incorporated into a solution or suspension. These preparations should contain at least 0.1% of active compound, but may be varied between 0.5 and about 30% of the weight thereof. The amount of active compound in such compositions is such that a suitable dosage will be obtained. Preferred compositions and preparations according to the present invention are prepared so that a parenteral dosage unit contains between 0.5 to 100 milligrams of active compound.

The solutions or suspensions may also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in disposable syringes or multiple dose vials made of glass or plastic.

Examples of the compounds of this invention include:
4-amino-7,8-dihydrothieno[2,3-b]quinolin-5(6H)-one;
4-amino-5,6,7,8-tetrahydrothieno[2,3-b]quinolin-5-ol;
4-benzylamino-7,8-dihydrothieno[2,3-b]quinolin-5(6H)-one;
4-benzylamino-5,6,7,8-tetrahydrothieno[2,3-b]quinolin-5-ol;
4-amino-1-methyl-5H-1,6,7,8-tetrahydropyrazolo[3,4-b]quinolin-5-ol;
4-benzylamino-1-methyl-5H-1,6,7,8-tetrahydropyrazolo[3,4-b]quinolin-5-one;
4-benzylamino-1-methyl-5H-1,6,7,8-tetrahydropyrazolo-[3,4-b]quinolin-5-ol;
5-amino-6,7,8,9-tetrahydrobenzo[b][1,7]naphthyridin-6-one;
5-amino-6,7,8,9-tetrahydrobenzo[b][1,7]naphthyridin-6-ol;
5-benzylamino-6,7,8,9-tetrahydrobenzo[b][1,7]naphthyridin-6-one; and
4-amino-7,8-dihydro-2,3-dimethylfurano[2,3-b]quinolin-5(6H)-one.

The following examples are presented for the purpose of illustrating this invention.

EXAMPLE 1

4-Amino-7,8-dihydrothieno[2,3-b]quinolin-5(6H)-one, maleate 2-(1-Oxo-2-cyclohexen-3-yl)amino-3-cyanothiophene (15.15 g) was suspended in 350 ml of tetrahydrofuran (THF) and thereafter 16.7 g of potassium carbonate and 0.7 g of cuprous chloride were added. The reaction mixture was brought to reflux and refluxed for a total of 7 hours (after 1 hour an additional 0.7 g of cuprous chloride was added). At the end of this time 100 ml of methanol was added to the reaction mixture and it was refluxed for additional 15 minutes and thereafter filtered. The filtrate was evaporated and then purified by flash chromatography (10% isopropanol/toluene). The product-containing fractions were evaporated and taken up in a minimum of hot isopropanol. The maleate salt was formed by adding a slight excess of maleic acid, allowing the salt to crystallize and then filtering the crystals. Recrystallization from methanol/ether gave 2.1 g of analytically pure maleate, mp 183°–184°.

ANALYSIS: Calculated for $C_{11}H_{10}N_2OS \cdot C_4H_4O_4$: 53.88% C; 4.22%H; 8.38%N; found: 53.74%C; 4.21%H; 8.34%N

EXAMPLE 2

4-Amino-5,6,7,8-tetrahydrothieno[2,3-b]quinolin-5-ol

4-Amino-7,8-dihydrothieno[2,3-b]quinolin-5(6H)-one (5.61 g) was suspended in 50 ml of dry tetrahydrofuran. After chilling with ice/water, 25 ml of 1M lithium aluminum hydride in tetrahydrofuran was added. The reaction was complete in 30 minutes. Saturated ammonium chloride solution was added (8 ml) and the precipitate, which contained both the product and aluminum salts, was filtered off. This precipitate was treated with 5% aqueous hydrochloric acid, giving first a solution and then a new precipitate. This was filtered off and taken up in warm methanol and the mixture was made basic with aqueous $NH_3$. The precipitated free base, free of aluminum salts, was filtered off and recrystallized twice from dimethylsulfoxide/water to give 2.1 g, mp 226° (d).

ANALYSIS: Calculated for $C_{11}H_{12}N_2OS$: 59.97%C; 5.49%H; 12.72%N; Found: 59.45%C; 5.51%H; 12.63%N

EXAMPLE 3

4-Benzylamino-7,8-dihydrothieno[2,3-b]quinolin-5(6H)-one

4-Amino-7,8-dihydrothieno[2,3-b]quinolin-5(6H)-one (6.21 g) was dissolved in 60 ml of dimethylsulfoxide (DMSO). Potassium hydroxide (2.3 g, calculated as 85%), which had been pulverized under pentane, was added to the reaction mixture. After 30 minutes 5.0 g of benzyl bromide was added, and after an additional 30 minutes, 1.0 g of potassium hydroxide and 2.0 g of benzyl bromide were added. After a total reaction time of 90 minutes, 200 ml of water was added to the reaction mixture, causing a gummy precipitate to separate. The crude product was collected by filtration and purified by flash chromatography (10% ethyl acetate/dichloromethane) followed by recrystallization from ethyl acetate. Obtained in this manner was 2.35 g of analytically pure product, mp 159°–160°.

ANALYSIS: Calculated for $C_{18}H_{16}N_2OS$: 70.10%C; 5.23%H; 9.09%N; Found: 70.15%C; 5.43%H; 9.05%N

EXAMPLE 4

4-Benzylamino-5,6,7,8-tetrahydrothieno[2,3-b]quinolin-5-ol

4-Benzylamino-7,8-dihydrothieno[2,3]bquinolin-5(6H)-one (2.63 g) was dissolved in 50 ml of dry tetrahydrofuran. To this solution was added 5.0 ml of 1M lithium aluminum hydride in tetrahydrofuran and then the reaction mixture was stirred for 45 minutes. At the end of this time 5 ml of saturated aqueous ammonium chloride was added and then the inorganic precipitate was filtered off. The filtrate was evaporated and the residue recrystallized from methanol/water to give 1.72 g of analytically pure product, mp 180°–181°.

ANALYSIS: Calculated for $C_{18}H_{18}N_2OS$: 69.64%C; 5.84%H; 9.03%N; Found: 69.92%C; 5.90%H; 8.89%N

EXAMPLE 5

4-Amino-1-methyl-5H-1,6,7,8-tetrahydropyrazolo[3,4-b]quionolin-5-one, maleate A suspension consisting of 5-(1-oxo-2-cyclohexen-3-yl)amino-1-methyl-4-cyanopyrazole (32.5 g), milled potassium carbonate (20.8 g), cuprous chloride (1.5 g) and 1,4-dioxane (500 ml) was heated at gentle reflux for 2.5 hours. At this time, another 5 g of potassium carbonate and 55 mg of cuprous chloride were added. This was heated for an additional 1.5 hours at which time 100 ml of methanol was added and the mixture was filtered. This was concentrated to one half the volume and 800 ml of water was added. This was then concentrated to a solid which was dissolved in methanol/dichloromethane and preadsorbed on silica.

The desired quinolinone was purified via flash chromatography (ethyl acetate) to give 13.9 g of a solid, mp 199°–214° C. A 4.5 g portion of the solid was then rechromatographed to give 3.7 g of a solid, mp 214°–218° C. This was recrystallized from tetrahydrofuran/hexane (1:1) to give 2.36 g of a powder, mp 218°–220° C. This was suspended in 50 ml of isopropanol and 1.1 equivalents of maleic acid was added. This was stirred for 2.5 hours, filtered and dried to give 2.25 g of a powder, mp 167°–169°.

ANALYSIS: Calculated for $C_{11}H_{12}N_4O.C_4H_4O_4$: 54.21%C; 4.85%H; 16.86%N; Found: 54.07%C; 4.98%H; 17.69%N

EXAMPLE 6

4-Amino-1-methyl-5H-1,6,7,8-tetrahydropyrazolo[3,4-b]quinolin-5-ol

To a cooled suspension of 4-amino-1-methyl-5H-1,6,7,8-tetrahydropyrazolo[3,4-b]quinolin-5-one (6.0 g) in 80 ml of tetrahydrofuran was added 27 ml of 1M lithium aluminum hydride in tetrahydrofuran. This was stirred for 45 minutes and then quenched with 15 ml of saturated ammonium chloride solution. An additional 20 ml of tetrahydrofuran and 50 ml of ethyl acetate were added and the inorganics were filtered. The organics were dried over anhydrous magnesium sulfate and preadsorbed on silica. The desired quinolinol was purified via flash chromatography (5% methanol/dichloromethane) to give 3.3 g of a powder, mp 149°–153° C. d. This was recrystallized from tetrahydrofuran/hexane (2:1) to give 1.9 g of a powder, mp 154°–157° C. d.

ANALYSIS: Calculated for $C_{11}H_{14}N_4O$: 60.53%C; 6.47%H; 25.67%N; Found: 60.38%C; 6.39%H; 26.29%N

EXAMPLE 7

4-Benzylamino-1-methyl-5H-1,6,7,8-tetrahydropyrazolo[3,4-b]quinolin-5-one, hemimaleate A suspension of 4-amino-1-methyl-5H-1,6,7,8-tetrahydropyrazolo[3,4-b]quinolin-5-one (9.5 g) in 85 ml of dimethylsulfoxide was treated with pulverized potassium hydroxide. To the resulting solution was added benzyl bromide (9.0 g). After 15 minutes, an additional 3 ml of benzyl bromide was added and this was stirred for 15 minutes. To the reaction flask was then added 200 ml of water. The precipitate was filtered, rinsed with water, and triturated with ether to give 9.7 g of a powder, mp 136°–153° C.

A portion of this product was further purified via flash chromatography (15% ethyl acetate/dichloromethane) to give a powder, mp 167°–171° C., which was suspended in isopropanol and treated with 10% excess of maleic acid. The mixture was stirred for 1.5 hours and filtered, and the solid product was dried to give an analytically pure powder, mp 176°–181° C. d.

ANALYSIS: Calculated for $C_{18}H_{18}N_4O.0.5C_4H_4O_4$: 65.92%C; 5.53%H; 15.38%N; Found: 65.72%C; 5.47%H; 15.33%N

EXAMPLE 8

4-Benzylamino-1-methyl-5H-1,6,7,8-tetrahydropyrazolo[3,4-b]quinolin-5-ol

To a cooled suspension of 4-benzylamino-1-methyl-5H-1,6,7,8-tetrahydropyrazolo[3,4-b]quinolin-5-one (3.9 g) in 70 ml of tetrahydrofuran was added 7 ml of 1M lithium aluminum hydride in tetrahydrofuran. This was stirred for 20 minutes and then quenched with 8 ml of saturated ammonium chloride solution. The reaction mixture was diluted with additional tetrahydrofuran, filtered and dried over anhydrous sodium sulfate.

The organics were then preadsorbed on silica and purified via flash chromatography (ethyl acetate) to give 2.9 g of a powder, mp 185°–189° C. This was recrystallized from 75 ml of tetrahydrofuran/hexane (2:1) to give 2.2 g of a floculent solid, mp 185°–187° C. d.

ANALYSIS: Calculated for $C_{18}H_{20}N_4O$: 70.10%C; 6.54%H; 18.17%N; Found: 70.11%C; 6.60%H; 18.24%N

EXAMPLE 9

5-Amino-6,7,8,9-tetrahydrobenzo[b][1,7]naphthyridin-6-one

A mixture consisting of 3-(1-oxo-2-cyclohexen-3-yl)amino-4-cyanopyridine (3.3 g), potassium carbonate (2.35 g), cuprous chloride (153 mg) and 80 ml of tetrahydrofuran was refluxed for 1 hour. To the mixture was added 25 ml of methanol and the inorganics were removed by filtration. The filtrate liquid was then passed through a packed column and eluted with ethyl acetate to give 3.0 g of solid, mp 237°–242° C. This was recrystallized from n-butyl acetate to give 1.85 g of crystals, mp 242.5°–245° C.

ANALYSIS: Calculated for $C_{12}H_{11}N_3O$: 67.59%C; 5.20%H; 19.71%N; Found: 67.59%C; 5.27%H; 19.73%N

EXAMPLE 10

5-Amino-6,7,8,9-tetrahydrobenzo[b][1,7]naphthyridin-6-ol

To a cooled solution of 5-amino-6,7,8,9-tetrahydrobenzo[b][1,7]naphthyridin-6-one (3.05 g) was added 14.5 ml of 1M lithium aluminum hydride in tetrahydrofuran. This was stirred for 1 hour.

The reaction was quenched with 12 ml of saturated ammonium chloride solution, the inorganics were filtered and the cake was stirred in methanol/dichloromethane. The combined organic filtrates were dried over anhydrous sodium sulfate and preadsorbed on silica. The alcohol was purified via flash chromatography (10% methanol/dichloromethane) to give 3.0 g of a fibrous solid. This was recrystallized from dimethylsulfoxide/water to give 1.49 g of an analytically pure solid, mp 201°–204° C. d.

ANALYSIS: Calculated for $C_{12}H_{13}N_3O$: 66.96%C; 6.09%H; 19.52%N; Found: 66.71%C; 6.16%H; 19.42%N

EXAMPLE 11

5-Benzylamino-6,7,8,9-tetrahydrobenzo[b][1,7]naphthyridin-6-one, maleate

To a solution of 5-amino-6,7,8,9-tetrahydrobenzo[b][1,7]naphthyridin-6-one (3.1 g) in 40 ml of dimethylsulfoxide was added pulverized potassium hydroxide. To this was then added benzyl bromide (2.1 ml). After 15 minutes, an additional 1 ml of benzyl bromide was added. This was stirred for 15 minutes and 150 ml of water was added. The resulting precipitate was filtered, rinsed with water, dissolved in dichloromethane and dried over anhydrous magnesium sulfate. This was preadsorbed on silica and purified via flash chromatography (15% isopropanol/toluene) to give 1.2 g of a solid, mp 175°–180° C. A portion of this was suspended in isopropanol and 1.1 equivalents of maleic acid was added. This resulting solid was filtered to give an analytically pure solid, mp 172°–173° C.

ANALYSIS: Calculated for $C_{18}H_{17}N_3O \cdot C_4H_4O_4$: 65.86%C; 5.05%H; 10.02%N; Found: 65.86%C; 5.22%H; 9.84%N

EXAMPLE 12

4-Amino-7,8-dihydro-2,3-dimethylfurano[2,3-b]quinolin-5(6H)-one

A suspension consisting of 2-(1-oxo-2-cyclohexen-3-yl)amino-3-cyano-4,5-dimethylfuran (11.1 g), potassium carbonate (7.3 g), cuprous chloride (476 mg) and 130 ml of 1,4-dioxane was heated at gentle reflux for 2 hours.

To the reaction mixture was added 50 ml of dichloromethane/methanol (1:1) and the inorganics were filtered. The organics were passed through a column of magnesium silicate (ethyl acetate) and were then preadsorbed on silica. The desired compound was purified via flash chromatography (7% isopropanol/toluene) to give 820 mg of a powder, mp 190°–198° C. d. A portion was recrystallized from ethyl acetate to give an analytically pure solid, mp 202°–205° d.

ANALYSIS: Calculated for $C_{13}H_{14}N_2O_2$: 67.81%C; 6.13%H; 12.17%N; Found: 67.53%C; 6.04%H; 12.08%N

We claim:

1. A compound of the formula

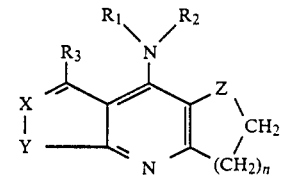

where =X—Y— is

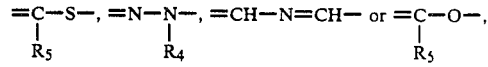

$R_4$ being loweralkyl and $R_5$ being hydrogen or loweralkyl, —Z— is

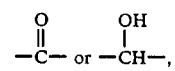

n is 1, 2 or 3, $R_1$ and $R_2$ are each independently hydrogen, loweralkyl or arylloweralkyl, and $R_3$ is hydrogen or loweralkyl, the term aryl signifying an unsubstituted phenyl group or a phenyl group substituted with 1, 2 or 3 substituent groups each of which being independently loweralkyl, halogen, loweralkoxy or trifluoromethyl, with the proviso that when =X—Y— is

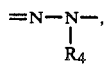

n is 2 or 3, $R_1$ is hydrogen and $R_2$ is hydrogen or loweralkyl, Z is not

or a pharmaceutically acceptable acid addition salt thereof.

2. The compound as defined in claim 1, where —Z— is

3. The compound as defined in claim 1, where $R_1$ is loweralkyl or arylloweralkyl.

4. The compound as defined in claim 3, where —Z— is

5. The compound as defined in claim 4, where n is 2.

6. The compound as defined in claim 1, where =X—Y— is

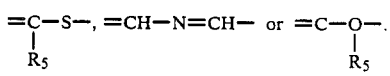

7. The compound as defined in claim 6, where n is 2.

8. The compound as defined in claim 1, which is 4-amino-7,8-dihydrothieno[2,3-b]quinolin-5(6H)-one.

9. The compound as defined in claim 1, which is 4-amino-5,6,7,8-tetrahydrothieno[2,3-b]quinolin-5-ol.

10. The compound as defined in claim 1, which is 4-benzylamino-7,8-dihydrothieno[2,3-b]quinolin-5(6H)-one.

11. The compound as defined in claim 1, which is 4-benzylamino-5,6,7,8-tetrahydrothieno[2,3-b]quinolin-5-ol.

12. The compound as defined in claim 1, which is 4-amino-1-methyl-5H-1,6,7,8-tetrahydropyrazolo[3,4-b]quinolin-5-ol.

13. The compound as defined in claim 1, which is 4-benzylamino-1-methyl-5H-1,6,7,8-tetrahydropyrazolo[3,4-b]quinolin-5-one.

14. The compound as defined in claim 1, which is 4-benzylamino-1methyl-5H-1,6,7,8-tetrahydropyrazolo[3,4-b]quinolin-5-ol.

15. The compound as defined in claim 1, which is 5-amino-6,7,8,9-tetrahydrobenzo[b][1,7]naphthyridin-6-one.

16. The compound as defined in claim 1, which is 5-amino-6,7,8,9-tetrahydrobenzo[b][1,7]naphthyridin-6-ol.

17. The compound as defined in claim 1, which is 5-benzylamino-6,7,8,9-tetrahydrobenzo[b][1,7]naphthyridin-6-one.

18. The compound as defined in claim 1, which is 4-amino-7,8-dihydro-2,3-dimethylfurano[2,3-b]quinolin-5(6H)-one.

19. A pharmaceutical composition comprising an effective memory enhancing amount of a compound as defined in claim 1 and a carrier therefor.

20. A method of treating a patient in need of memory enhancement which comprises administering to the patient an effective memory enhancing amount of a compound as defined in claim 1.

* * * * *